United States Patent [19]
Peterson

[11] Patent Number: 5,178,005
[45] Date of Patent: Jan. 12, 1993

[54] SAMPLE SLEEVE WITH INTEGRAL ACOUSTIC TRANSDUCERS

[75] Inventor: Paul E. Peterson, San Francisco, Calif.

[73] Assignee: Western Atlas International, Inc., Houston, Tex.

[21] Appl. No.: 546,872

[22] Filed: Jul. 2, 1990

[51] Int. Cl.[5] .......................... G01H 5/00; E21B 49/00
[52] U.S. Cl. ........................................ 73/153; 73/597; 73/760
[58] Field of Search ................ 73/153, 38, 19.03, 597, 73/598, 760, 799, 818, 819, 821, 596

[56] References Cited

U.S. PATENT DOCUMENTS

| | | | |
|---|---|---|---|
| 3,537,541 | 11/1970 | Desai et al. | 73/153 |
| 3,587,297 | 6/1971 | Kammer | 73/597 |
| 3,995,501 | 12/1976 | Wiley | 73/597 |
| 4,253,327 | 3/1981 | Wiley | 73/38 |
| 4,573,342 | 3/1986 | Jones | 73/38 |
| 4,599,981 | 7/1986 | Braver et al. | 73/38 |
| 4,627,270 | 12/1986 | Jones | 73/38 |
| 4,631,963 | 12/1986 | Sprunt et al. | 73/597 |
| 4,713,968 | 12/1987 | Yale | 73/597 |
| 4,864,846 | 9/1989 | Jones | 73/38 |

Primary Examiner—Hezron E. Williams
Assistant Examiner—Michael Brock
Attorney, Agent, or Firm—E. Eugene Thigpen

[57] ABSTRACT

An apparatus is provided for determining the acoustic anisotropy of a sample being subjected to simulated in-situ pressures and/or temperatures. A sample of the formation of interest is received by a compliant sleeve disposed in a pressure chamber. The compliant sleeve houses a plurality of transducers which are placed in intimate contact with the sample upon pressurization of the pressure chamber. When the pressure chamber reaches the desired pressure and/or temperature, the transducers are energized. The travel times of the generated acoustic signals through the sample are recorded to determine the anisotropic behavior of the sample. The velocity variations of the sample can indicate the historical principal stress axes of the formation at depth.

13 Claims, 3 Drawing Sheets

SAMPLE SLEEVE WITH INTEGRAL ACOUSTIC TRANSDUCERS

BACKGROUND OF THE INVENTION

1. Field of the Invention

The present invention relates to an apparatus for measuring the acoustic anisotropy of materials, and particularly to an apparatus for determining the acoustic anisotropy of a material while under increased pressure and temperature.

2. Discussion of the Related Art

In the oil and gas industry, once a well has been drilled and shows the presence of oil or gas, a determination is made on whether it would be economical to produce. A primary factor in determining whether a well may be economical is the flow rate of the product from the formation into the well. For marginally economic wells, the flow rate may be enhanced by fracturing the reservoir formation to expose more surface area of the formation to the well bore. The orientation of induced fractures in a formation may depend upon the amount of overburden, the formation's principal stress axes, bedding planes, formation homogeneity or cementation. In some cases the principal stress axes control the orientation of fractures.

Generally, fracture planes induced in the formation occur in the plane of the two greatest principal stress axes. For example, if the greatest principal stress axis of a formation is along the vertical plane, fractures induced in the formation most likely will occur in some vertically oriented plane. Orientation of in-situ principal stress axes can sometimes be determined by measuring the velocity anisotropy of samples taken from the subsurface interval of interest. The technique is based on the theory that an acoustic pulse propagates through a homogenous material of unit dimension at the same velocity along all axes. If the stress is greater along one of the other axes and then relieved, microfractures will sometimes develop in planes substantially perpendicular to that stress axis. The presence of microfractures generally decreases the effective velocity of acoustic waves propagating through the material. Thus it has been found that acoustic velocity can be lower along the axis of greatest stress.

Traditionally the engineer would determine the acoustic anisotropy of a formation by extracting an oriented core sample from the reservoir formation. At least two additional smaller samples were taken from the larger core along different axes. Each small sample, having the same dimensions, would be placed between two transducers. One transducer would generate an acoustic signal in the sample. This pulse would travel through the core and be detected by the other transducer at the opposite end. The differences in the acoustic wave travel time through the two samples can reveal the orientation of past stress axes. A major disadvantage with the traditional technique is that the samples were measured at ambient pressure and temperature which provides incomplete data sets. Additionally, a separate sample was required for a minimum of three measurement directions, thus requiring an inordinate amount of time and expense.

There has been a long felt, yet unsolved need, for a method and apparatus for measuring the acoustic anisotropy of a single sample. Moreover there has been a long felt need for a method and apparatus for measuring the acoustic velocity of a sample under conditions substantially similar to those experienced by the sample in nature.

SUMMARY OF THE INVENTION

This instant invention provides an apparatus for measuring the acoustic velocity, and determining any anisotropy, using a single sample while subjected to a range of pressures and temperatures. The material to be sampled is placed in a pressure chamber and surrounded by a compressible sleeve which is then sealed at each end. The orientation of the principle axes of the sample and the dimensions are noted. Moreover, it is preferred that the sample be of a shape so as to conform with the internal shape of the compressible sleeve.

The compressible sleeve contains a plurality of transducers radially disposed at known intervals. This may include transducers which are diametrically opposed. Additionally, a transducer may be located at each end of the sample. Each transducer is integral with the wall structure of the sleeve and connected by electrical conductors to an external recording and control unit. The sleeve and transducers are in turn surrounded by a fluid tight material to maintain the integrity of the pressure chamber.

Pressurization of the chamber by both radial and axial pressure forces the compressible sleeve to conform tightly about the sample and the sealed end to press against the ends of the sample. At the desired pressure, and temperature the transducers may be energized to produce a discreet signal which propagates through the sample and is received by a generally opposing transducer. The travel time of the signal through the sample is recorded. This process is repeated along a desired number of axes passing through the sample. The collected data are analyzed and used to determine the past principle stress axes of the sample.

BRIEF DESCRIPTION OF THE DRAWING FIGURES

A better understanding of the benefits and advantages of my invention may be obtained from the appended detailed description and drawing figures, wherein.

DETAILED DESCRIPTION OF A PREFERRED EMBODIMENT

FIGS. 1 through 4 generally illustrate a device 10 in which the invention may be employed for testing desired characteristics of a material. Construction and operating details of such a device may be found in greater detail in U.S. Pat. Nos. 4,573,342, 4,627,270 and 4,864,846, all of which are incorporated herein by reference. Although the instant invention has application to a great many materials, for the purposes of this disclosure, the discussion will be limited to the analysis of earthen samples.

Figure 1:
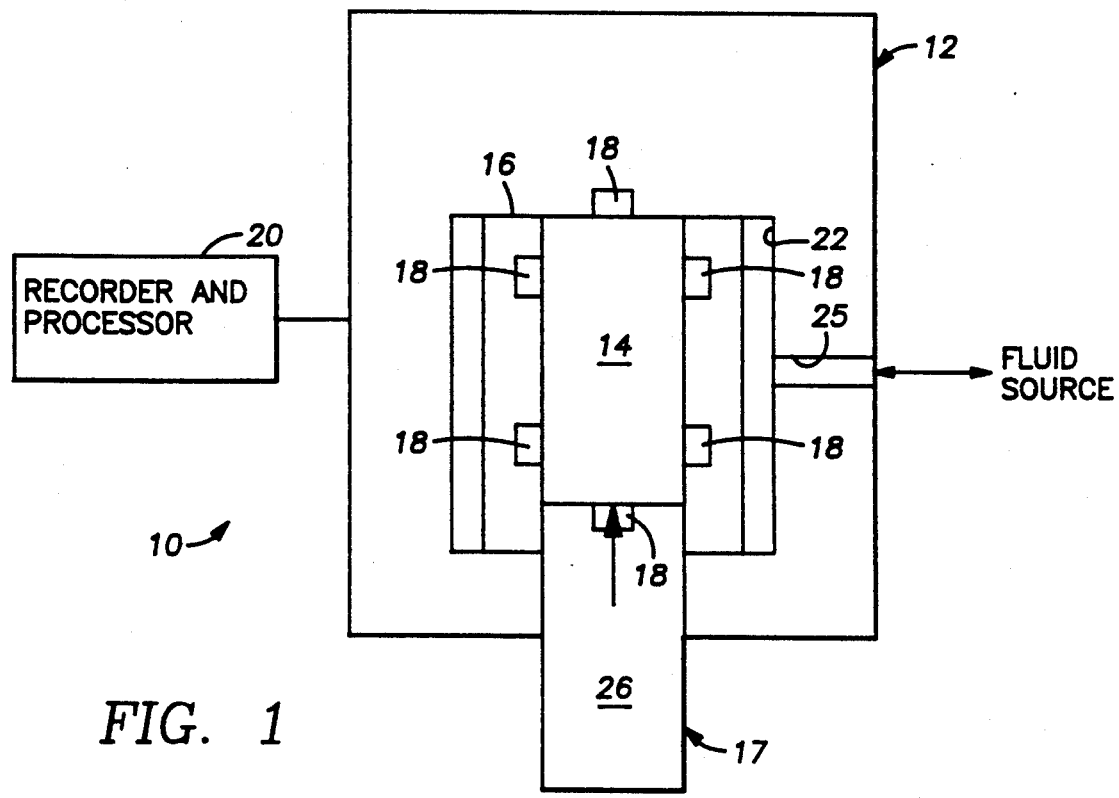
FIG. 1 is a schematic diagram of the instant invention.

FIG. 1 is a schematic diagram of the instant invention as employed in a device 10 used to measure the permeability and porosity of samples. The device 10 includes a sample holder 12 for receiving the material 14 to be tested. Disposed within the holder 12 is a chamber 22 with means 16 and 17 for applying a radial and axial stress respectively to the material 14. Radial stress may be applied by a cylindrical sleeve 36 discussed in greater detail below and a fluid introduced thereabout through a port or passage 25 coupled to a fluid source. The axial stress on the sample may be applied by a piston 26 which is also discussed below. Enclosed within the holder 12 are means 18, integral with the radial stress applicator 16, for generating and receiving acoustic signals in the material 14. A remote device 20 is operably coupled to the generating and receiving means to gather, store and process data from the generating and receiving means 18.

Figure 3:
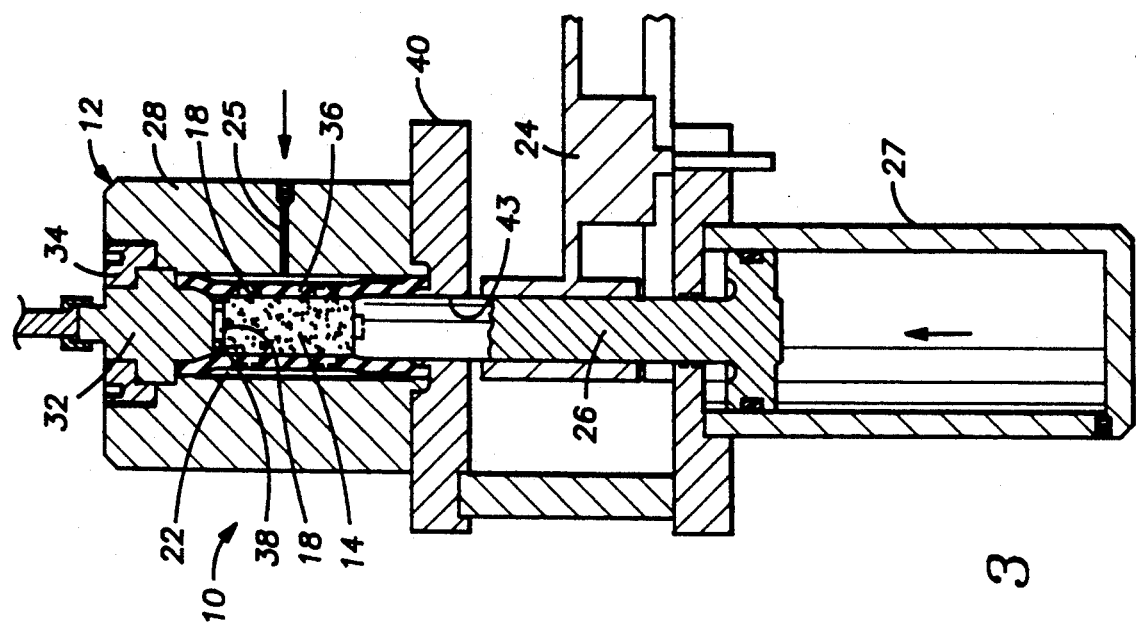
FIGS. 2 and 3 are elevational views of the device and means for loading samples into the device.
Figure 2:
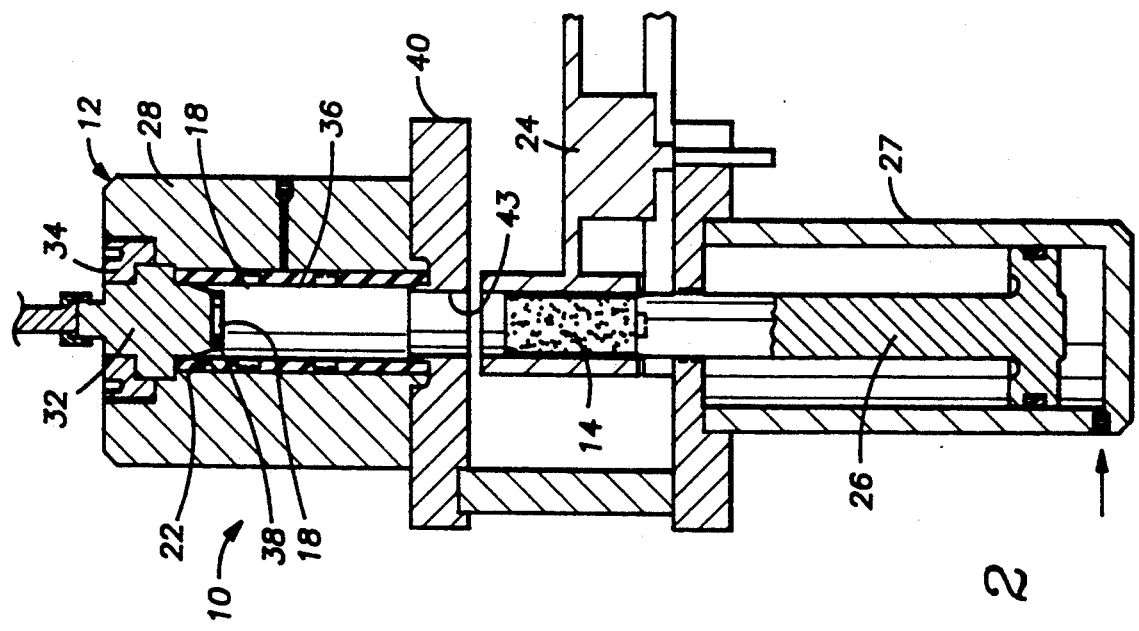

FIGS. 2 and 3 are elevational views of the sample holder 12 and a means 26, 27 for loading the samples into the holder. The apparatus may have a carousel 24 capable of carrying a plurality of samples 14 of substantially constant diameter but of varying length. A piston 26 disposed within a cylinder 27 may be located beneath the carousel 24 for selectively raising one of the samples from the carousel 24 into the sample holder 12 as shown in FIG. 3. Once the material is loaded in the holder 12, the piston 26 and the sample holder 12 cooperate together to form a test cell or pressure chamber 22 about the held sample. The pressure chamber and piston function simultaneously to apply both axial and radial forces to the sample, simulating the overburden forces experienced in its natural environment.

Figure 4:
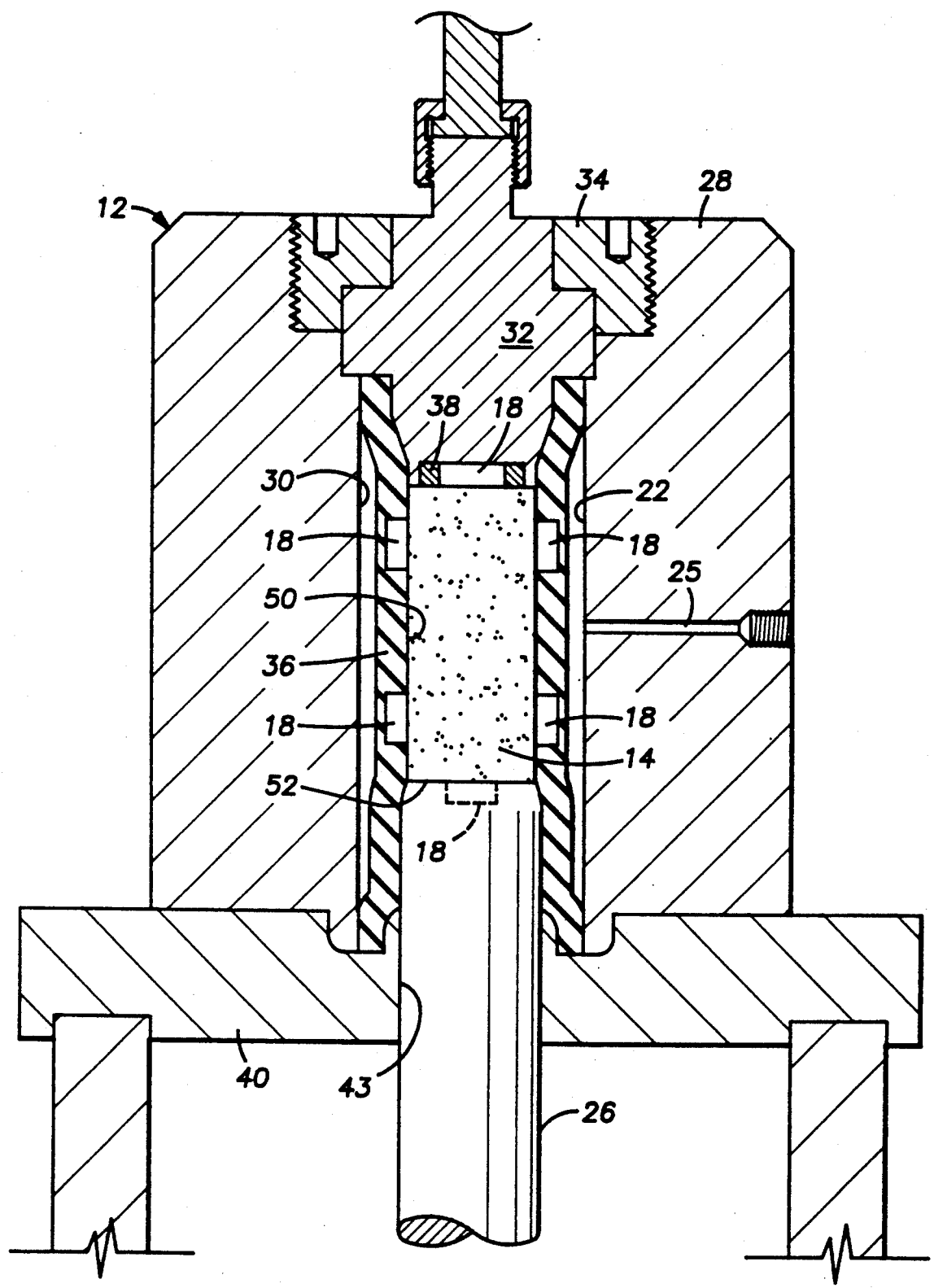
FIG. 4 is an enlarged diagram of the pressure chamber containing the instant invention.

FIG. 4 is an elevational view of the sample holder 12 exhibiting the instant invention. The sample holder 12 is comprised of a mass or body 28 having an axial bore 30. The axial bore is closed at one end by an upper plug 32. Fixed to the lower end of the upper plug 32 may be a perforated plate 38. An upper retainer plug 34 anchored to the body 28 by bolts or threads secures the plug 32 within the body. The rubber sleeve 36 mentioned above is coaxially disposed within the bore 30, and has one end sealed about an end of the upper plug.

At the bottom of the body 28 and sealing the lower end of the rubber sleeve 36 is a support plate 40. The support plate 40 contains a hole 43 aligned with the axial bore 30 and may be secured to the body by way of bolts. The axial bore 30, plug 32, support plate 38, and an end 52 of the piston 26 essentially define the pressure chamber 22. The components comprising the sample holder 12 are preferably cast or machined from stainless steel or high-strength aluminum.

In one embodiment of the instant invention, a plurality of transducers 18 may be integrally located within the walls of the rubber sleeve 36. Each transducer within the sleeve 36 has a corresponding transducer diametrically located opposite thereto, all of which are designed to emit and to receive acoustic pulses. The emitted pulses are transmitted through the sample surrounded by the sleeve 36. Measurement of the transmission time, together with the known path length, allows calculation of the transmission velocity. Alternatively, at least two transducers may be placed at each desired radial location about the inside of the sleeve 36: one crystal to generate and receive compressional waves and another crystal to generate and receive shear waves. Shear waves and compressional wave propagate through various media at different velocities and aid the scientist in the evaluation of materials. It may be desirable that additional transducers, similar to sensors 18 located in the rubber sleeve 36, be located in the upper plate 38 and in the end 52 of the piston 26. Transducers located about the circumference of the sample and at each end allow velocity calculations for substantially all axes of the sample, thus providing better data sampling and consequently a better estimate of the principle stress axes of the formation nature.

Sleeve 36 may be manufactured from rubber or other flexible material adapted to isolate the sample from a pressure medium such as a gas or fluid introduced into the pressure chamber. For high temperature operations (28° C. to over 200° C.), Viton sleeves may be used. For low temperature operations (temperatures below 65° C.), the rubber sleeve may be used. The thickness of the sleeve 36 may vary depending upon the pressure and temperature extremes contemplated to be encountered. A sleeve thickness on the order of three-sixteenths of an inch has proven suitable. Other thicknesses and compositions may be found to be suitable and are considered to be within the scope of this invention.

Figure 5:
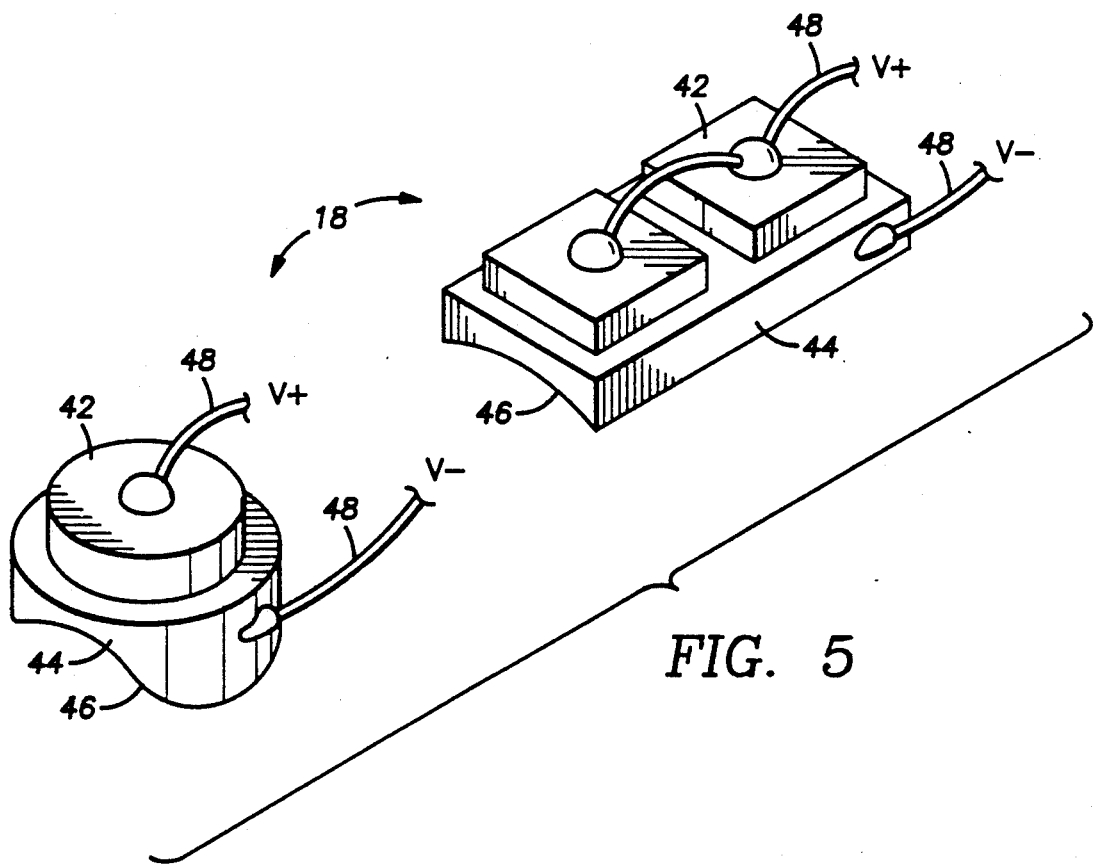
FIG. 5 is a perspective view of two transducers contemplated by this invention.

FIG. 5 is a perspective view of one embodiment of a transducer 18 which may be employed in the invention. The transducers 18, located in the wall of the rubber sleeve 36, preferably are piezoelectric-crystals 42 mounted to a high-strength substrate 44. The crystals 42 may be any of a wide variety of piezoelectric materials including the PZT-5A made by Valpey-Fisher Company. Transducers can be chosen to operate at any practical range of frequencies. Typically a frequency on the order of 1 megahertz (MHz) is used. To assure good acoustic coupling of the acoustic signal with the sample, the substrate 44 may have one side contoured 46 so as to conform to the inner wall 50 (FIG. 4) of the rubber sleeve 36 (FIG. 4).

As suggested earlier the transducers are incorporated in the wall of the rubber sleeve 36. This may be readily accomplished by molding the sleeve 36 around the transducers or embedding the transducer in a cavity formed in the rubber sleeve 36 to accommodate each transducer 18. Electrical conductors 48 from each transducer pass through the sleeve 36 to join other conductors 48 at a desired location before exiting the sample holder 12.

In operation, the material 14 may be loaded into the sample holder 12 by the piston 26 so that an upper end of the sample is urged against the upper end plug plate 38. The end 52 of the piston 26 may also be received within the rubber sleeve 36. Once the sample is loaded, a fluid is introduced through port 25 in the sample holder to the outside of the sleeve causing the sleeve to collapse and conform to the circumference of the sample. The pressure also places the transducer substrate 44 in intimate contact with the sample.

The application of pressure to the sample simulates the overburden conditions existing in the formation. With the pressure stabilized, each transducer is energized in any desired pattern, transmitting a pulse into the sample. Each acoustic pulse propagates through the sample and is detected, the travel time of which is recorded for later reference. The process is repeated for substantially all of the transducers located in the pressure chamber. If more than one wave type is generated, e.g. compressional wave and shear waves, the travel time differences between the two waves are also recorded for later reference. It should be noted that no particular sequence is required for the generation of the acoustic pulses, only that the respective axes or radial of propagation be known for each signal.

Once the acoustic velocity measurements of a sample have been completed, additional measurements may be performed on the sample such as the porosity and permeability. Conversely, such measurements may be performed simultaneously or prior to the velocity calculations.

My invention has been described with a certain degree of specificity. Variations will occur to those skilled in the art which are within the scope and spirit of this invention which is limited only by the appended claims, wherein:

I claim as my invention:

1. An apparatus for measuring a transit time of an acoustic signal through a sample under pressure greater than ambient atmospheric pressure, comprising:
   (a) a pressure chamber;
   (b) compliant means disposed within the chamber and adapted to receive the sample;
   (c) means integral with the compliant means for generating and receiving acoustic signals through the sample; and
   (d) means operably coupled to the generating and receiving means for measuring the transit time of the acoustic signals through the sample.

2. The apparatus as defined in claim 1, wherein the means for generating and receiving acoustic signals through the sample comprises:
   (a) a plurality of transducers, at least two of which are diametrically opposed to each other and recessed within the compliant means.

3. The apparatus as defined in claim 1, wherein the means for generating and receiving acoustic signals through the sample comprises:
   (a) a plurality of transducers diametrically opposing each other about the perimeter of the sample.

4. The apparatus as defined by claim 1, wherein the pressure chamber comprises:
   (a) a body having a cylindrical bore extending therethrough;
   (b) a plug disposed at one end of the bore and closing the end thereof to define a cavity;
   (c) at least one passage extending through the body and in fluid communication with the cavity; and
   (d) means for introducing a fluid under pressure into the cavity.

5. The apparatus as defined by claim 1, wherein the compliant means comprises a sleeve concentrically received within the chamber.

6. The apparatus as defined by claim 1, wherein the means integral with the compliant means for generating and receiving acoustic signals comprises a plurality of transducers adjacent the sample, the transducers capable of generating and receiving P wave and S wave acoustic signals.

7. The apparatus as defined by claim 1, wherein the means operably coupled to the generating and receiving means for measuring the transit time of the acoustic signals, comprises a computer.

8. The apparatus as defined by claim 1, further comprising means disposed at each end of the sample for generating and receiving acoustic signals in the sample.

9. An apparatus for measuring an acoustic velocity in an earthen core sample, comprising:
   (a) means for producing a pressure greater than ambient atmospheric pressure and adapted to receive the core sample;
   (b) a sleeve disposed within the producing means and partially surrounding the core sample;
   (c) means, integral with the sleeve, for generating and receiving acoustic signals through the core sample; and
   (d) means, operably coupled to the generating and receiving means, for measuring a transit time of the acoustic signals through the core sample.

10. The apparatus for measuring the acoustic velocity in a core sample as defined by claim 9, wherein the means for producing a pressure greater than ambient atmospheric pressure comprises a pressure chamber adapted to receive the sample, the pressure chamber being in fluid communication with a pressure medium introduced to the pressure chamber by a pumping means.

11. The apparatus as defined by claim 9, further comprising means disposed at each end of the core sample for generating and receiving acoustic signals in the core sample.

12. The apparatus as defined by claim 9, wherein the means for generating and receiving acoustic signals in the core sample comprise piezoelectric sensors.

13. The apparatus as defined by claim 12, wherein the piezoelectric sensors generate and receive compressional waves and shear waves.

* * * * *